US008052459B2

(12) United States Patent
Smith et al.

(10) Patent No.: US 8,052,459 B2
(45) Date of Patent: Nov. 8, 2011

(54) DUAL DIRECTIONAL CONNECTOR

(75) Inventors: Kyle Smith, Foothill Ranch, CA (US);
Farshid Dilmaghanian, Foothill Ranch, CA (US)

(73) Assignee: Bal Seal Engineering, Inc., Foothill Ranch, CA (US)

(*) Notice: Subject to any disclaimer, the term of this patent is extended or adjusted under 35 U.S.C. 154(b) by 0 days.

(21) Appl. No.: 12/792,648

(22) Filed: Jun. 2, 2010

(65) Prior Publication Data
US 2010/0311266 A1 Dec. 9, 2010

Related U.S. Application Data

(60) Provisional application No. 61/184,624, filed on Jun. 5, 2009.

(51) Int. Cl.
*H01R 13/62* (2006.01)
(52) U.S. Cl. ........................................ 439/372
(58) Field of Classification Search .......... 439/345, 439/372, 489, 953, 346–347
See application file for complete search history.

(56) References Cited

U.S. PATENT DOCUMENTS

| 5,791,930 | A  | * | 8/1998  | Tabata et al. ............ 439/345 |
| 6,638,098 | B2 | * | 10/2003 | Yamaoka ................ 439/489 |
| 6,725,096 | B2 | * | 4/2004  | Chinn et al. ............ 607/115 |
| 6,913,480 | B2 | * | 7/2005  | Wilcox ................... 439/372 |
| 7,914,315 | B2 | * | 3/2011  | Kuhn et al. ............. 439/345 |
| 2002/0122690 | A1 |   | 9/2002  | Poon et al. |
| 2004/0005802 | A1 | * | 1/2004  | Lamirey ................. 439/345 |
| 2008/0254670 | A1 |   | 10/2008 | Balsells et al. |
| 2008/0255631 | A1 |   | 10/2008 | Sjostedt et al. |

FOREIGN PATENT DOCUMENTS

| GB | 2 194 298 A | 3/1988 |
| WO | WO 03/067713 A1 | 8/2003 |

* cited by examiner

*Primary Examiner* — Jean Duverne
(74) *Attorney, Agent, or Firm* — Klein, O'Neill & Singh, LLP

(57) ABSTRACT

A connector is provided that permits locking between a pin and a housing a canted coil spring yet permit separation by allowing turning of the canted coil spring so that the canted coil spring can compress along the minor axis. In one example, the connector incorporates two grooves on the pin to allow the rotation. In another example, the connector incorporates two grooves in the bore of the housing to allow the rotation. The connector may be used in a number of applications or industries, such as for aerospace, automotive, and medical device industries, to name a few.

27 Claims, 2 Drawing Sheets

DUAL DIRECTIONAL CONNECTOR

CROSS-REFERENCE TO RELATED APPLICATION

This is a regular utility application of Provisional Application Ser. No. 61/184,624, filed Jun. 5, 2009; the contents of which are expressly incorporated herein by reference.

FIELD OF ART

Locking and/or latching mechanisms are generally discussed herein with particular reference to those that are cylindrical and that utilize canted coil springs with specific groove geometries in connecting parts to achieve locking and/or latching with a built in release feature. Applications for the disclosed mechanisms include mechanical connections with optional electrical transmission. Other applications include in-line connectors, such as for a header of an implantable medical device.

BACKGROUND

Conventional connection mechanisms utilize a canted coil spring and specific groove geometries to achieve locking and/or latching. In the case of locking, the device becomes permanently locked, meaning that removal can only occur by permanently damaging the canted coil spring. In the case of latching, the device can be unlatched but includes a single removal force. Locking is achieved between two mating parts (e.g., cylindrical part or shaft and housing) where a tapered bottom groove exists in the housing and holds an axial spring and where the tapered bottom groove aligns with a corresponding groove on the cylindrical part which accepts the spring. The tapered bottom groove is configured in such a way that the spring compresses along the minor access upon insertion but not upon removal. If a user unwisely attempts to unlatch the latching device anyway, the spring will be forced to compress along its major axis upon removal, which permanently damages the spring due to the characteristics of a canted coil spring only allowing an insignificant compression along the major axis.

For a typical application, upon insertion of the cylindrical part, such as a shaft or a pin, into a bore of a housing, the entry edge of the cylindrical part comes into contact with the axial spring and causes the spring to rotate in the tapered bottom groove. This also pushes the spring coils into the deeper region of the tapered bottom groove, allowing room for the coils to compress along the minor axis. Once the corresponding groove in the cylindrical part comes in contact with the spring, the spring has more room available to uncompress or relax along the minor axis causing the spring to fall into the corresponding groove with the spring maintaining a small amount of compression in a holding state. Removal of the cylindrical part would force the canted coil spring to rotate in the opposite direction, forcing the major axis of the coils to rotate towards the shallow end of the tapered bottom groove. Due to the corresponding groove in the inserted part exhibiting a holding effect, it is not possible for the spring to rotate properly to allow for removal because this requires a significant amount of deflection along the major axis. However, the only foreseeable outcome with this approach is for the spring to damage, thus resulting in a mechanical lock.

SUMMARY

Aspects of the present device, system, and method include provisions to permit a connector for locking applications to be disconnected without permanently damaging the canted coil spring. During use, the spring is located in a primary groove to lock a pin to a housing. In one embodiment, the connector is provided with a sufficiently deep secondary groove to allow the canted coil spring to rotate back to its relaxed vertical position. Unlike when the spring is located in the primary groove, the spring is not held when it is located in the secondary groove and has room to rotate in the opposite direction, much like during insertion.

In one example, the leading edge of the secondary groove makes contact with the canted coil spring and rotates it in the tapered bottom groove along the minor axis towards the shallow end allowing for removal of the canted coil spring from the secondary groove into the first groove. Here the canted coil spring is orientated so that the cylindrical part can be completely unlatched from the housing.

Thus, once the cylindrical part is inserted into the housing and engages the primary groove, the canted coil spring experiences a removal lock. To unlatch, the cylindrical part is first inserted further into the housing. In one example, when the pin is further inserted, a secondary groove located on the pill moves into the housing so that the spring engages the secondary groove. In a specific example, the second groove is larger than the first groove. Once in the larger second groove, the spring is able to rotate and be unlatched by moving the cylindrical part in the removal direction, opposite the insertion direction. By larger, the groove can have a larger groove depth, a larger volumetric space, or both.

A still further feature of the present device, system, and method is understood to include a connector comprising a pin located inside a bore of a housing by inserting the pin into the bore of the housing in a first direction; preventing the pin from moving in a second direction, opposite the first direction, by positioning a spring located inside a groove defined by a housing groove and a primary groove on the pin; and wherein the pin is permitted to move in the second direction by first further moving the pill in the first direction before it could be moved in the second direction. In a particular embodiment, the canted coil spring located inside the first groove of the pin is rotated and moves to a second groove on the pin before the pin is able to move in the second direction.

In addition, the larger secondary groove following the primary groove can provide a lower removal force as compared to removal from the primary groove in latching applications.

An exemplary connector provide herein is understood to comprise a housing comprising a bore comprising a housing groove comprising a housing groove depth. A pin comprising a pin groove comprising a pin depth is disposed in the bore of the housing. A canted coil spring is retained within a connector groove defined by the housing groove and the pin groove in a first spring position. The connector further comprises a second groove for accommodating the canted coil spring located adjacent at least one of the housing groove and the pin groove.

An exemplary method provided herein is understood to comprise a method for mating a pin in a bore of a housing. In certain examples, the method comprising the steps of moving the pin, which comprises a first pin groove and a second pin groove, in a first direction and locking the pin to the housing by preventing withdrawal of the pin in a second direction, which is opposite the first direction. The housing comprising a housing groove. The method further comprising positioning a canted coil spring concurrently in the first pin groove and the housing groove at a first turn angle so that a major axis of the canted coil spring is compressed to move the pin in the second direction. The method further comprising moving the pin in the first direction into the bore of the housing from a first position relative to the housing to a second position relative to the housing to locate the canted coil spring in the second pin groove. The method still further comprising moving the pin in the second direction after positioning the canted coil spring in the second pin groove so that the canted coil spring is repositioned in the first pin groove.

The device is further understood to include a connector comprising a housing comprising a bore and a housing groove and a pin comprising a first pin groove having a first groove depth and a second pin groove comprising a second groove depth, which is larger than the first groove depth. The connector wherein a canted coil spring is engageable with the first pin groove to lock the pin to the housing, and wherein the canted coil spring is engageable with the second pin groove to permit rotation of the canted coil spring to allow separation of the pin from the housing.

SUMMARY OF THE DRAWINGS

The various embodiments of the present connectors, systems, and associated methods now will be discussed in detail with an emphasis on highlighting the advantageous features. These embodiments depict the novel and non-obvious connector shown in the accompanying drawings, which are for illustrative purposes only. These drawings include the following, FIGs., in which like numerals indicate like parts.

DETAILED DESCRIPTION

Figure 1:
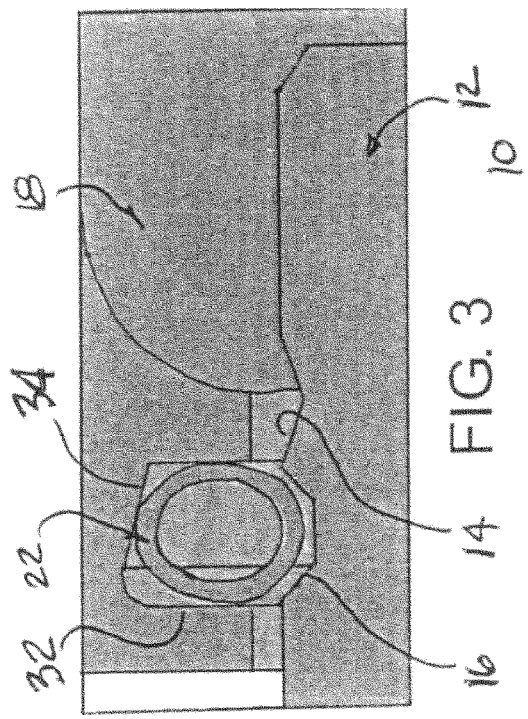
FIG. 1 shows a schematic cross-sectional side view of a dual direction connector, which shows a pin moving into a bore of a housing.

The following detailed description describes the present embodiments with reference to the drawings. In the drawings, reference numbers label elements of the present embodiments. These reference numbers are reproduced below in connection with the discussion of the corresponding drawing features.

The embodiments of the present connectors, systems, and associated methods are described below with reference to the figures. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unit or a unitary piece and whereas a unitary piece means a singularly formed single piece, such as a singularly formed mold or cast. Still further, the terms "first" and "second" used herein are understood as identifiers only to distinguish between similar but different components. Thus, unless the context indicates otherwise, "first" and "second" are not limiting terms.

FIG. 1 shows a partial cross-sectional side view of a connector provided in accordance with aspects of the present device, system and method, which is generally designated 10. The connector is symmetrical about a center line of the pin 12. In one example, the pin 12, also referred to as a shaft or a cylindrical insert, comprises a primary groove 14 and a secondary groove 16. The pin preferably incorporates a tapered nose section 11 to facilitate insertion of the pin into a bore of the connector housing 18. In the example shown, the primary groove 14 comprises a bottom wall having a depth measured from the pin outer surface of D1 and the secondary groove 16 comprises a bottom wall having a depth measured from the pin outer surface of D2. In a particular example, the secondary groove 16 is larger than the primary groove 14 and D2 is greater than D1.

The pin 12 is shown being inserted into the stationary housing 18, which has a housing groove 20 and a canted coil spring 22 being disposed therein. The spring 22 is angled and compressed upon insertion caused by contact with the entry 11 of the cylindrical insert 12. The spring 22 has a major axis, defined by the larger axis of the coil, and a minor axis, defined by the smaller axis of the coil, which is perpendicular to the major axis. In one example, the pin has a round cross-section. In other embodiments, the pin has a square cross-section, an oval cross-section, or a polygon cross-section.

The housing groove 20 comprises a first sidewall 30, a second sidewall 32, and a bottom wall 34, which is preferably tapered or angled relative to either of the two sidewalk. In one example, the bottom wall 34 tapers downwardly in the direction of insertion, also sometimes referred to as the first direction.

Figure 2:
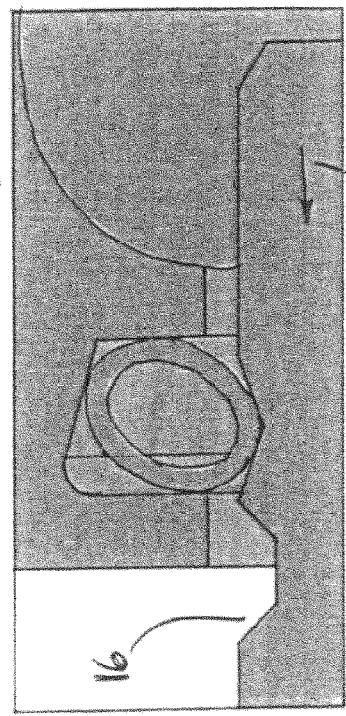
FIG. 2 shows a schematic cross-sectional side view of the dual direction connector of FIG. 1 in which the pin is secured in the housing by positioning a canted coil spring in a groove defined by the housing and the pin.

FIG. 2 shows the spring 22 located in the initial or primary groove 14 in the cylindrical part 12 and the housing groove 20. In this position, as in traditional locking applications, removal of the cylindrical part 12 would require the spring 22 to compress along the major axis, which if carried out would require a relatively large force and cause the spring to be permanently damaged. In one example, the spring 22 is rotated so that its major axis, defined by the longer dimension of the spring, faces the tapered wall surface 36 of the primary groove 14 and between sidewall 32 and tapered bottom surface 34 of the housing groove 20. In this configuration, the normally non-compressible major axis needs to collapse in order to permit removal of the pin 12 in a second direction, opposite to the first direction 24 (FIG. 1). However, such compression is not possible without damaging the spring.

Figure 3:
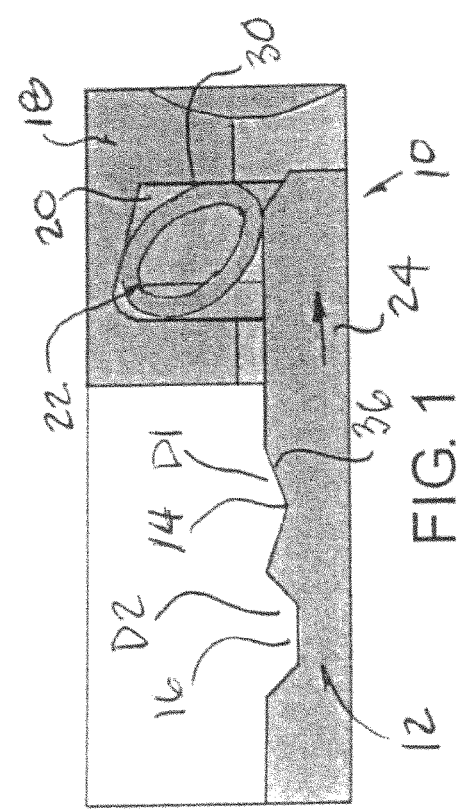
FIG. 3 shows a schematic cross-sectional side view of the dual direction connector of FIG. 2 wherein the spring is moved to a second groove defined by the housing and the pin and rotated.
Figure 4:
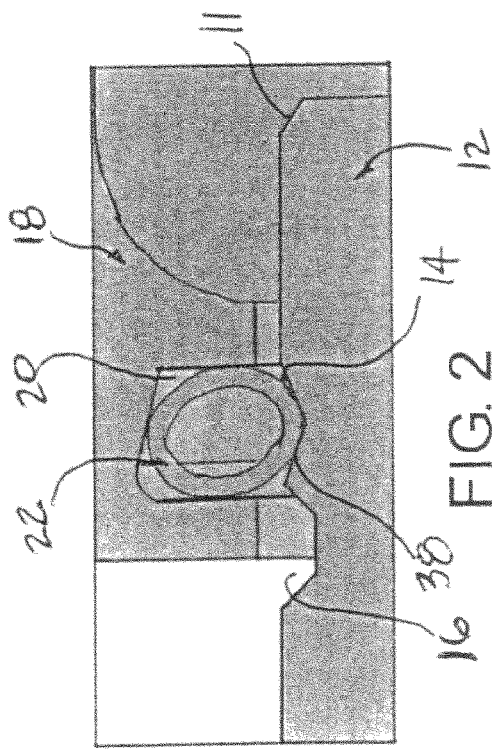
FIG. 4 shows a schematic cross-sectional side view of the dual direction connector of FIG. 3 wherein the pin is moved in a second direction and the spring moves from the second pin groove back into the first pin groove in the direction of the arrow.

FIG. 3 shows the spring 22 being moved beyond the initial groove 14 by moving the cylindrical part 12 further into the housing 18 in the direction of the arrow 24 of FIG. 1, i.e., further in the first direction. As the spring 22 is already turned in the first direction in its normal operating turn angle, further insertion of the pin in the first direction 24 is permitted. In one example, the second tapered wall surface 38 of the primary groove 14 is angled to exert a force in the direction of the minor axis of the spring, which is orthogonal to the major axis, to permit further movement in the first direction. In one example, the primary groove 14 comprises a V-groove. The spring 22 now latches into the secondary groove 16 and the housing groove 20. The secondary groove 16, being deeper and larger than the initial groove 14, does not maintain contact with the spring 22 and the spring is allowed to relax and straighten out. In other embodiments, the secondary groove 16 does contact the spring but also provides sufficient depth for the spring to relax and straighten out. From this point, the cylindrical part 12 can be removed since the spring 22 has room to rotate in the opposite direction, similar to performing an insertion in the opposite direction, and properly compress along the minor axis back into the first groove 14 as the pin is withdrawn. FIG. 4 shows the spring rotated in a correct orientation that allows the assembly to unlatch when moving in the second direction 26, which is opposite the first direction. Further movement of the pin in the second direction 26 from the perspective of FIG. 4 will permit complete removal from the housing 18.

Thus, an aspect of the present device, system and method is understood to include a connector comprising a cylindrical insert comprising a first groove having a first groove depth and a second groove comprising a second groove depth, which is larger than the first groove depth, and wherein a spring is engageable with the first groove to lock the cylindrical insert with a housing comprising a housing groove, and wherein the spring is engageable with the second groove to permit rotation of the spring to allow separation of the cylindrical insert from the housing.

A further aspect of the present device, system, and method is understood to include a method for inserting a cylindrical insert into a bore of a housing in a first direction and locking the cylindrical insert to the housing by preventing withdrawal of the cylindrical insert in a second direction, opposite the first direction. Said method comprising inserting said cylindrical insert, which comprises a first groove and a second groove, into the housing in a first direction to position a spring in the first groove and preventing removal of the cylindrical insert in the second direction by turning the spring to require compressing the spring along a major axis. The method further comprising moving the cylindrical insert in the first direction into the housing from a first position relative to the housing to a second position relative to the housing to position the spring in the second groove. The method further comprising moving the cylindrical insert in a second direction to re-position the spring in the first groove and removing the cylindrical insert from said housing such that the cylindrical insert is no longer located in a bore of the housing.

A further aspect of the present device, system, and method is a cylindrical insert comprising an insertion end, a first groove located proximate the insertion end, and a second groove located proximate the first groove and further away from the insertion end than the first groove, and wherein the first groove comprises a first depth and the second groove comprises a second depth, which is deeper than the first depth. Depth is a relative term and is understood to mean with reference to the outer surface of the pin along a nominal outer diameter of the pin.

A still further aspect of present device, system, and assembly is a connector comprising a pin comprising a first groove and a second groove and a housing comprising a housing groove. The pin is configured to be inserted into a bore of the housing when moving in a first direction. The device, system, and assembly wherein a spring is configured to be positioned between the first groove and the housing groove in a first position, between the second groove and the housing groove in a second position, and between the first groove and the housing groove in a third position. The device, system, and method wherein when the spring is in the first position, the pin is locked to the housing and removal of the pin from the housing by moving the pin in a direction opposition to the first direction is prevented without compressing the spring along its major axis. The device, system, and method wherein when the spring is in the second position, the spring is rotated from a turned angle from when the spring is in the first position. The device, system, and method wherein when the spring is in the second position, the spring does not contact the housing groove. In one example, the spring is in a second turned angle when in the second position. The device, system, and method wherein when the spring is in the third position, the spring is rotated to a third turned angle.

In yet another aspect of the present device, system, and method, a pin is provided comprising a single groove comprising a tapered bottom surface and two sidewall surfaces that are parallel to one another. The device, system, and method further comprising a housing comprising bore comprising a first housing groove located near an inlet opening and a second housing groove located adjacent the first housing groove and further away from the inlet opening than the first housing groove. The device, system, and method, wherein the second housing groove is larger than the first housing groove. In one example, the first housing groove has a depth D1 and the second housing groove has a depth D2, both measured relative to an inside nominal diameter of the bore; and wherein D2 is deeper or larger than D1. In an embodiment, the first housing groove incorporates the groove geometry of the primary pin groove 14 and the second housing groove incorporates the groove geometry of the secondary pin groove 16.

In one example, the housing 18 is made from a metallic material. In another example, the metallic material, which may be a highly conductive metal such as aluminum, aluminum alloys, copper, copper alloys, noble metals, noble metal alloys, or silver, is coated with an outer conductive material. For example, the inner metal layer may be coated or plated with an outer stainless steel layer, which has high tensile strength than the inner metal layer. In another embodiment, the inner conductive layer is made from a high tensile strength material, such as stainless steel, and the out coated or plated material is made from a highly conductive material, such as aluminum, aluminum alloys, copper, copper alloys, noble metals, noble metal alloys, or silver. In another embodiment, the canted coil spring 22 and optionally the pin 12 are made from multi-metallic materials having material combinations discussed herein. Exemplary bi-metallic and multi-metallic connectors are disclosed in co-pending application Ser. No. 12/767,421, filed Apr. 26, 2010, and US Publication No. 2008/0254670, the contents of which are expressly incorporated herein by reference. In another application, for non-electrical transmission, the housing 18 is made from a thermoplastic or an engineered plastic material.

Exemplary applications for the connectors disclosed herein include aerospace industry, for automotive industry, for oil and gas industry, for consumer electronics industry, for medical device industry, and for green technology, such as for wind mill and solar panel applications. For these industries, the disclosed system, device, and method may be used to connect wires or cables together.

Figure 5:
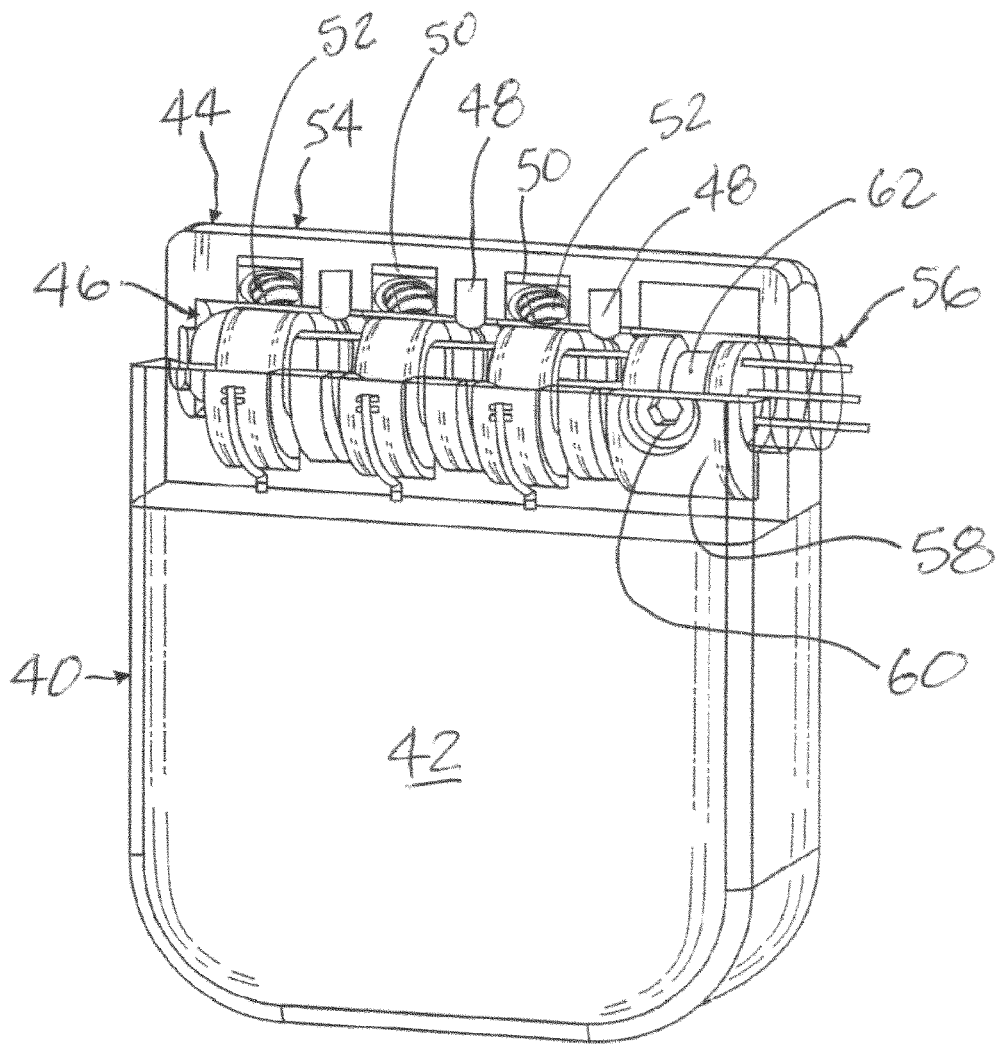
FIG. 5 is a partial cut-away perspective view of an implantable medical device comprising a sealed housing and an in-line connector located in a header.

Turn now to FIG. 5, a schematic partial cut-away perspective view of an implantable medical device (IMD) is shown, which can include implantable cardio defibrillators, pacemakers, and programmable neurostimulator pulse generators. The IMD comprises a sealed housing 42, which is known in the industry as a can or canned housing, and a header 44 comprising an in-line connector 46. The in-line connector 46 comprises a plurality of alternating seal elements 48 and conductive elements 50, of which only three alternating sets are shown. Canted coil springs 52 are also incorporated, one in contact with each of the conductive elements 50. The header housing 54, the springs 52, the conductive elements 50, and the seal elements 48 have a common bore for receiving, a lead cable 56. The lead cable 56 has terminal ends (not shown) that are positioned near an area to be treated, such as near the heart for a cardiac heart pacemaker application. The cable 56 is configured to carry signals away from the canned housing 42 or vice versa for a therapeutic monitoring application. Additional information regarding IMDs and in-line connectors are disclosed in US Publication numbers 2008/0246231 and 2008/0255631, which are expressly incorporated herein by reference. Other IMDs and in-line connectors are also disclosed in co-pending application Ser. Nos. 12/717,732, filed Mar. 4, 2010, and 12/618,493, filed Nov. 13, 2009, the contents of each of which are expressly incorporated herein by reference.

To secure the lead cable 56 within the bore of the header, a retention block 58 is used, which comprises a set screw 60 for fastening against a corresponding surface 62 on the lead cable, which is analogous to a pin groove. The retention block 58 may be located at the inlet of the header 44, as shown, or at the far end of the header. In accordance with an aspect of the present device, system, and method, the connector 10 of FIGS. 1-4 is used in place of a combination retention block 58 and pin groove 62 on a lead cable 56 of a header of an IMD. For example, the housing 18 of FIGS. 1-4 may be used in place of the retention block 58 of FIG. 5 and instead of a single pin groove 62, a primary groove and a secondary groove are used for the lead cable, similar to that shown on the pin 12 of FIGS. 1-4. Furthermore, the connector may be placed near the inlet as shown in FIG. 5 or at the far end of the header. Still furthermore, the modified retention mechanism may incorporate a single pin groove on the lead cable and two housing grooves for the retention block, as discussed above in the alternative configuration.

The above description presents the best mode contemplated for carrying out the present connectors, systems, and associated methods, and of the manner and process of making and using them, in such full, clear, concise, and exact terms as to enable any person skilled in the art to which it pertains to make and use these connectors, systems, and associated methods. These connectors, systems, and associated methods are, however, susceptible to modifications and alternate constructions from that discussed above that are fully equivalent. Consequently, these connectors, systems, and associated methods are not limited to the particular embodiments disclosed. On the contrary, these connectors, systems, and associated methods cover all modifications and alternate constructions coming within the spirit and scope of the connectors, systems, and associated methods as generally expressed by the following claims, which particularly point out and distinctly claim the subject matter of the connectors, systems, and associated methods.

What is claimed is:

1. A connector comprising:
   a housing comprising a bore comprising a housing groove comprising a housing groove depth;
   a pin comprising a pin groove comprising a pin depth disposed in the bore of the housing,
   a canted coil spring retained within a connector groove defined by a combination of the housing groove and the pin groove in a first spring position; the canted coil spring, being movable relative to both the housing and the pin; and
   a second groove for accommodating the canted coil spring when the canted coil spring moves to a second spring position inside said bore, said second groove located adjacent the housing groove or the pin groove.

2. The connector of claim 1, wherein the second groove is located on the pin and adjacent the pin groove.

3. The connector of claim 2, wherein the second groove comprises a second groove depth, which is larger than the pin depth.

4. The connector of claim 2, wherein the second groove is larger than the pin groove.

5. The connector of claim 1, wherein groove is located in the bore of the housing, adjacent the housing groove.

6. The connector of claim 5, wherein the second groove comprises a second groove depth, which is larger than the housing groove depth.

7. The connector of claim 5, wherein the second groove is larger than the housing groove.

8. The connector of claim 1, wherein at least one of the housing groove and the pin groove comprises a groove configuration comprising a tapered bottom wall and two parallel sidewalls.

9. The connector of claim 1, wherein the canted coil spring is rotatable relative to the housing by rotating from a first turn angle when in the first spring position to a second turn angle when in the second spring position.

10. The connector of claim 9, wherein the pin is movable in a first direction but not a second, opposite, direction when the canted coil spring is in the first spring position.

11. The connector of claim 10, wherein the pin is movable in the second direction when the canted coil spring is in the second spring position.

12. The connector of claim 1, wherein the second groove has a different configuration than the connector groove and the pin groove.

13. A connector comprising a housing comprising a bore and a housing groove and a pin comprising a first pin groove having a first groove depth and a second pin groove comprising a second groove depth; wherein a canted coil spring is engageable with the first pin groove and the housing groove to secure the canted coil spring at a first spring angle, and wherein the canted coil spring is engageable with the second pin groove and the housing groove to permit rotation of the canted coil spring to a second spring angle, which is different from the first spring angle.

14. The connector of claim 13, wherein the first pin groove has a different configuration than the second pin groove.

15. The connector of claim 13, wherein the second groove depth is relatively deeper or larger than the first groove depth.

16. The connector of claim 13, wherein the housing groove comprises a groove configuration comprising a bottom wall and two sidewalls.

17. The connector of claim 16, wherein the two sidewalls are generally parallel to one another.

18. The connector of claim 17, wherein the bottom wall is angled relative to the two sidewalls.

19. A connector comprising:
   a housing comprising a bore and a housing groove having a housing groove configuration;
   a pin comprising a pin groove having a pin groove configuration;
   a canted coil spring disposed in the bore in a first spring position defined by a combination of the housing groove and the pin groove;
   a second groove located adjacent the housing groove or the pin groove, the second groove having a second groove configuration that differs from the housing groove configuration and the pin groove configuration; and
   wherein the canted coil spring is movable relative to the pin and the housing.

20. The connector of claim 19, wherein the second groove is located on the pin and adjacent the pin groove.

21. The connector of claim 19, wherein the second groove is located in the bore of the housing, adjacent the housing groove.

22. The connector of claim 19, wherein the canted coil spring is rotatable relative to the housing by rotating from a first turn angle when in the first spring position to a second turn angle when in a second spring position, which is defined at least in part by the second groove.

23. The connector of claim 19, wherein the pin is movable in a first direction but not a second, opposite, direction when the canted coil spring is in the first spring position.

24. The connector of claim 23, wherein the pin is movable in the second direction when the canted coil spring is in a second spring position, which is defined at least in part by the second groove.

25. The connector of claim 19, wherein the housing groove configuration comprises a bottom wall and two sidewalls.

26. The connector of claim 25, wherein the two sidewalls are generally parallel to one another.

27. The connector of claim 26, wherein the bottom wall is angled relative to the two sidewalk.

* * * * *

UNITED STATES PATENT AND TRADEMARK OFFICE
CERTIFICATE OF CORRECTION

PATENT NO. : 8,052,459 B2  
APPLICATION NO. : 12/792648  
DATED : November 8, 2011  
INVENTOR(S) : Kyle Smith et al.

Page 1 of 1

It is certified that error appears in the above-identified patent and that said Letters Patent is hereby corrected as shown below:

On the Cover Page, item (57), in Abstract, in column 2, line 2, delete "a canted" and insert -- using a canted --, therefor.

In column 4, line 34, delete "sidewalk." and insert -- sidewalls. --, therefor.

In column 7, line 62, in Claim 1, delete "spring," and insert -- spring --, therefor.

In column 8, line 8, in Claim 5, delete "wherein" and insert -- wherein the second --, therefor.

In column 10, line 10, in Claim 27, delete "sidewalk." and insert -- sidewalls. --, therefor.

Signed and Sealed this  
First Day of May, 2012

David J. Kappos  
*Director of the United States Patent and Trademark Office*